United States Patent
Marshall

(10) Patent No.: US 8,530,209 B2
(45) Date of Patent: *Sep. 10, 2013

(54) METHOD FOR PRODUCING PROBIOTICALLY DERIVED COMPOUNDS

(75) Inventor: Robert J. Marshall, Round Rock, TX (US)

(73) Assignee: Premier Research Labs, LP, Austin, TX (US)

( * ) Notice: Subject to any disclaimer, the term of this patent is extended or adjusted under 35 U.S.C. 154(b) by 864 days.

This patent is subject to a terminal disclaimer.

(21) Appl. No.: 11/028,272

(22) Filed: Jan. 3, 2005

(65) Prior Publication Data

US 2005/0118694 A1 Jun. 2, 2005

Related U.S. Application Data

(63) Continuation-in-part of application No. 10/722,777, filed on Nov. 26, 2003.

(51) Int. Cl.
*C12P 7/40* (2006.01)
*C12P 1/00* (2006.01)

(52) U.S. Cl.
USPC ............................................ 435/136; 435/41

(58) Field of Classification Search
USPC .................................................. 435/136, 41
See application file for complete search history.

(56) References Cited

U.S. PATENT DOCUMENTS

| | | | |
|---|---|---|---|
| 3,037,016 A | 5/1962 | Barker | |
| 4,245,048 A | 1/1981 | Hata et al. | |
| 4,769,329 A * | 9/1988 | Cooper et al. | 435/139 |
| 6,080,401 A | 6/2000 | Reddy et al. | |
| 6,368,617 B1 | 4/2002 | Hastings et al. | |
| 6,806,069 B2 | 10/2004 | Chokshi | |
| 6,867,024 B2 | 3/2005 | Chokshi | |
| 2002/0034815 A1 * | 3/2002 | Blank et al. | 435/252.3 |
| 2003/0095959 A1 | 5/2003 | Mayne | |

FOREIGN PATENT DOCUMENTS

| | | | |
|---|---|---|---|
| EP | 1 273 664 | | 1/2003 |
| JP | 2002-65199 A | * | 3/2002 |
| WO | WO 02/085293 | * | 10/2002 |

OTHER PUBLICATIONS

Ron S. Jackson "Wine Science: Principles, Practice, Perception" (2nd edition) p. 338 Apr. 2000.*
Glenn R. Gibson, M. B. Roberfroid "Colonic microbiota, nutrition, and health" Published by Springer, 1999 ISBN 0412798808, 9780412798801 p. 44.*
Sandrine Ollagnier-de Choudens et al. "Iron-Sulfur Center of Biotin Synthase and Lipoate Synthase" Biochemistry 2000, 39, 4165-4173.*
Derick Han et al. "HPLC of Reduced and Oxidized Lipoic Acid" Methods in Enzymology, vol. 251, 1995 pp. 315-325.*
E. Meucci et al. "Amino acids and plasma antioxidant capacity" Amino Acids (1997) 12:373-377.*
George A. Somkuti et al. "Permeabilization of *Streptococcus thermophilus* and *Lactobacillus delbrueckii* subsp. *bulgaricus* with Ethanol" Current Microbiology vol. 36 (1998), pp. 202-206.*
JPO Machine Translation of JP2002-065199A, 2002, pp. 1-14.*
Cronan et al. "Function, Attachment and Synthesis of Lipoic Acid in *Escherichia coli*" Advances in Microbial Physiology 2005; 50 () : 103-46 103-46.*
Horst Schuette and Maria-Regina Kula "Pilot- and Process-Scale Techniques for Cell Disruption" Biotechenology and Applied Biochemistry 12, 599-620 (1990).*
Meganathan R., "Ubiquinone Biosynthesis in Microorganisms", FEMS Microbiology Letters, 2001, vol. 203, p. 131-139.
Kawamukai M., "Biosynthesis, Bioproduction and Novel Roles of Ubiquinone", J. of Bioscience and Bioengineering, 2002, vol. 94, No. 6, p. 511-517.
Quiles J.L., et al., "*Curcuma longa* Extract Supplementation Reduces Oxidative Stress and Attenuates Aortic Fatty Streak Development in Rabbits", Arteriosclerosis, Thrombosis and Vascular Biology, 2002, vol. 22, p. 1225-1231.
E.M. Lansford, "Reversal by Ribonucleosides of Bacterial Growth Inhibition Caused by Alcohol," The Journal of Biological Chemistry, 1960, pp. 3551-3554, vol. 235, No. 12, American Society for Biochemistry and Molecular Biology, U.S.
L.J. Reed, "A Trail of Research from Lipoic Acid to alpha-Keto Acid Dehydrogenase Complexes," The Journal of Biological Chemistry, 2001 pp. 38329-38336, vol. 276, No. 42, American Society for Biochemistry and Molecular Biology, U.S.
J.J. Diwan, "Pyruvate Dehydrogenase & Krebs Cycle," 2007, pp. 1-8, located at http://www.rpi.edu/dept/bcbp/molbiochem/MBWeb/mb1/part2/krebs.htm (last accessed Nov. 10, 2009).
R.J. Marshall, "Stabilized DHLA (Dihydrolipoic Acid)," Nov. 2003, pp. 1-2.
R. Hermann et al., "Enantioselective pharmacokinetics and bioavailability of different racemic alpha-lipoic acid formulations in healthy volunteers," European Journal of Pharmaceutical Sciences, 1996, pp. 167-174, vol. 4, No. 3, Elsevier, Ireland.

(Continued)

*Primary Examiner* — Jon P Weber
*Assistant Examiner* — Thane Underdahl
(74) *Attorney, Agent, or Firm* — Amin Talati, LLC; Janine A. Moderson; Jonathan J. Krit

(57) ABSTRACT

A method for producing naturally derived beneficial compounds including dispersing a microbiological culture media including at least one live probiotic organism, and at least one nutraceutical and/or at least one nutritive agent in distilled water to form a broth, incubating the broth at a predetermined temperature for a select period of time to induce probiotic activity; halting the probiotic activity, and separating the desired compound from the broth.

28 Claims, No Drawings

(56) References Cited

OTHER PUBLICATIONS

A. Mercenier et al., "Probiotics as Biotherapeutic Agents: Present Knowledge and Future Prospects," Current Pharmaceutical Design, 2003, pp. 175-191, vol. 9, No. 2, Bentham Science Publishers, Netherlands.

C. Dunne et al., "Probiotics: from myth to reality. Demonstration of functionality in animal models of disease and in human clinical trials," Antonie van Leeuwenhoek, 1999, pp. 279-292, vol. 76, Kluwer Academic, Netherlands.

Vanden Boom, T. J., et al., "Lipoic Acid Metabolism in *Escherichia coli*: Isolation of Null Mutants Defective in Lipoic Acid Biosynthesis, Molecular Cloning and Characterization of *E. coli* lip Locus, and Identification of Lipoylated Protein of the Glycine Cleavage System," Journal of Bacteriology, 1991, p. 6411-6420, vol. 173, No. 20, American Society for Microbiology.

* cited by examiner

METHOD FOR PRODUCING PROBIOTICALLY DERIVED COMPOUNDS

This application is a continuation-in-part of U.S. patent application Ser. No. 10/722,777 filed on 26 Nov. 2003.

FIELD OF THE INVENTION

The present invention relates to a method for producing beneficial compounds for use in a medicament and/or a nutritional supplement. More particularly the present invention relates to a method for producing beneficial compounds derived from a once living source.

BACKGROUND OF THE INVENTION

Over the past few decades the medical, pharmaceutical and nutritional industries have demonstrated an increased interest in the use of traditional herbal and/or homeopathic medicines for the treatment and/or prevention of a variety of diseases, as well as for maintenance of good health and bodily function. Advances in the fields of biology, chemistry and medicine have allowed researchers to more closely and accurately study the impact and effects of various compounds on the human body and its myriad of metabolic and physiological processes. Such advances have led to an improved understanding of the uptake of many compounds such as, for example, nutrients, vitamins, minerals and other naturally occurring or synthetic compounds, and the role these compounds play in the day to day functioning of the body.

One area of study has focused on understanding the physiological effects of reactive oxygen species (ROS). ROS are byproducts of the normal metabolic processes of living organisms. ROS include oxygen-derived free radicals and non-radical derivatives that can cause oxidative damage to biological structures. ROS have also been shown to play a role in the aging process and a number of pathological syndromes such as, for example, diabetes. However, oxidative damage caused by ROS can be reduced or prevented through a number of mechanisms such as, for example, the use of antioxidants that can react directly with ROS in the body.

Green tea (*Camellia sinensis*) has been found to contain significant levels of polyphenols which have been found to be particularly potent antioxidants. Ingestion of such green tea polyphenols has been associated with heart disease and cancer prevention and may effectively reduce the incidence and severity of rheumatoid arthritis. However, green tea also contains alkaloids including caffeine, theobromine, and theophylline which provide a stimulant effect that may negatively impact a variety of neurological and cardiovascular processes.

Melatonin, a hormone naturally produced in the body by the pineal gland, is another particularly important antioxidant. One of the potential causes of age-related brain deterioration is toxic free radical compounds that are produced during aerobic metabolism. Vitamin E and Vitamin C aid in protecting the brain from oxidative stress by scavenging toxic free radicals. Recent studies have shown, however, that in vitro melatonin is more efficient than vitamin E in neutralizing certain free radical compounds such as, for example, the peroxyl radical. Other studies have indicated that the antioxidant properties of melatonin may inhibit tumor growth factor production and may augment the anti-tumor activity of Interleukin 2 in connection with certain types of cancer. Melatonin may also play a role in the regulation of sleep patterns and menopausal symptoms. However, most commercially available melatonin supplements contain synthetic or impure forms of pineal melatonin and may contain other herbs, such as valerian and chamomile, amino acids and various minerals.

Another area of particular interest and study is the use of supplements to boost energy and repair cells. Although required in minute amounts, B vitamins are essential for normal metabolism and enzyme function in the human body. B vitamins are the critical structural components of several key coenzymes such as, for example, thiamine pyrophosphate, flavin mononucleotide, flavin adenine dinucleotide, pyridoxal pyrophosphate, nicotinamide adenine dinucleotide, nicotinamide adenine dinucleotide phosphate, biotin, folic acid, cobalamin, coenzyme A and CoQ-10, and play a vital role in the breakdown of carbohydrates, fats and proteins, the synthesis of amino acids and other substances that comprise DNA and RNA, formation of red blood cells, the promotion of growth and development, and the production of energy. Individuals consuming a balanced diet generally ingest sufficient amounts of the B vitamins to meet the body's needs. Unfortunately, consumption of a balanced diet is not necessarily easily achieved in today's fast paced society. Therefore, many people turn to supplements such as B vitamins or more preferably the coenzymes derived from B vitamins to meet their needs.

Interest in traditional herbal medicines and homeopathic remedies has also peaked in the last several decades and much research has gone into the study of the physiological effects and benefits of the use of such traditional medicines and remedies. One such herbal remedy of interest is Chinese gold coin weed or herb that may be used to treat or prevent stone formation in the gall bladder. Chinese gold coin weed, alternatively known as herba lysimachiae, jinquiancao or yellow willow herb, has been used for thousands of years in China to treat liver, gallbladder, kidney and urinary bladder aliments. This herb contains phenolic ingredients, sterols, flavinoids, amino acids, tannin, volatile oils, choline and potassium salts. The whole plant has cholagogue (bile stimulating), depurative and diuretic properties that promote discharge of bile from the common bile duct which may soften and promote discharge of bile stones from the gallbladder.

The key to the effectiveness of ingestion of any of the above mentioned compounds depends on both the dosage ingested and the bioavailability of the particular compound. Bioavailability of a particular compound determines the body's ability to take up or absorb the compound and utilize the compound in physiological and metabolic processes. In general, if the bioavailability of a particular compound is low a larger dosage of the compound must be ingested to achieve the desired effect on the body. However, ingesting higher doses of some of compounds may cause undesirable side effects which may negatively impact other metabolic and physiological processes.

Thus, there is a need and a demand for beneficial compounds such as, for example, polyphenols, melatonin, vitamin B derived coenzymes, and herba lysimachiae which are derived from a natural source. In particular there is a need and a demand for beneficial compounds that are derived from a once living source that have an improved level of bioavailability. There is a further need and demand for a method of producing such beneficial compounds for use in a medicament or a nutritional supplement.

SUMMARY OF THE INVENTION

A general object of the invention is to provide a method for producing beneficial compounds for use in a medicament or a nutritional supplement.

A particular object of the invention is to provide a method for producing compounds derived from a once-living source that have improved bioavailability.

A more specific object of this invention is to overcome one or more of the problems described above.

The general object of the invention can be attained, at least in part, through a method for producing probiotically derived beneficial compounds including dispersing a microbiological culture media including at least one live probiotic organism, and at least one nutraceutical and/or at least one nutritive agent in distilled water to form a broth, incubating the broth at a predetermined temperature for a select period of time to induce probiotic activity; adding organic ethanol to halt the probiotic activity, and separating the desired compound from the broth.

The general art has generally failed to provide a method for producing beneficial compounds such as, for example, polyphenols, melatonin, vitamin B derived coenzymes and herba lysimachiae that is effective as desired in satisfying one or more of the above-identified performance criteria. Additionally, the prior art has generally failed to provide a method for deriving a beneficial compound from a once-living source such as by feeding a probiotic organism a nutraceutical or nutritive agent and separating the beneficial compound from the waste byproduct. Moreover, the prior art has generally failed to identify a microbiological culture media that can be utilized to produce such beneficial compounds.

The invention further comprehends a microbiological culture media for producing such beneficial compounds including: at least one live probiotic organism; and at least one nutritive or nutraceutical agent.

Other objects and advantages will be apparent to those skilled in the art from the following detailed description taken in conjunction with the appended claims.

DETAILED DESCRIPTION OF THE INVENTION

The present invention provides a method for producing a probiotically derived beneficial compound for use in a medicament or a nutritional supplement such as by feeding a probiotic organism a nutraceutical or nutritive agent, harvesting the waste byproducts and separating the beneficial compound from the waste byproducts. The present invention further provides beneficial compounds derived from a once living source having improved bioavailability and suitable for use in a medicament or a nutritional supplement.

As noted above, many compounds that may be used to assist or enhance metabolic and/or physiological processes in the body are derived from synthetic sources or are ingested in a synthetic form. However, it has been found that such synthetic or synthetically derived compounds may not have as high as desired level of bioavailability when ingested and may include additional compounds. To compensate for the lower than desired level of bioavailability such compounds are typically ingested in higher than normal dosages. Unfortunately, ingesting an increased dosage of these compounds may cause undesirable side effects particularly when the compound of interest is ingested with additional compounds that negatively or undesirably impact other metabolic or physiological processes. For example, green tea includes significant levels of polyphenols which have been found to be particularly potent antioxidants. However, green tea also includes significant levels of caffeine and theobromine. Thus, while increased consumption of green tea provides increased levels of polyphenols to scavenge free radicals and other reactive oxygen species (ROS) from the body, increased consumption of green tea also provides increased consumption of caffeine and theobromine which can have an undesirable impact on the nervous and cardiovascular systems.

Other synthetically derived compounds may not be in the best form for absorption by the body. For example, CoQ-10 is a B vitamin derived coenzyme that is a vital component of the mitochondria of all cells, particularly those of the heart and liver, and is co-factor in the transport of electrons between cells. Studies have shown that CoQ-10 is a potent antioxidant which scavenges free radicals and regenerates vitamin E in the cell membrane which may promote improved cardiovascular and immune system health. However, most commercially available CoQ-10 supplements contain oxidized CoQ-10 or UVI-quinone. When such oxidized CoQ-10 is ingested the body must expend energy to transform UVI-quinine to UVI-quinol or reduced CoQ-10 before the cells can absorb and utilize the reduced CoQ-10 in regenerative and electron transport processes.

Other beneficial compounds in their natural forms may simply be too difficult for the human body to digest in order to obtain the most desirable dosage. For example, Chinese gold coin weed or herba lysimachiae is an herb that is difficult for the human body to digest. Thus, repeated doses of the compound are required over extended periods of time in order to achieve the desired result.

Furthermore, some beneficial compounds are available in their synthetic form due to the unavailability of or cost of obtaining the natural compound. For example, melatonin, a hormone produced by and derived from the pineal gland of various animal species such as, for example, bears, is widely available in the synthetic form due to cost of extracting the hormone from pineal glands and public outcry against sacrificing living animals to obtain the hormone.

In accordance with certain preferred embodiments of the invention a beneficial compound for use in a medicament or a nutritional supplement is derived from a once living source. In particular such beneficial compound can be derived from a microbiological culture media including at least one live probiotic organism and at least one nutraceutical or nutritive agent.

While various live probiotic organisms may be included in the microbiological culture media of the invention, in accordance with certain preferred embodiments, the at least one probiotic organism can be selected from *Lactobacillus* species, *Bifidobacterium* species, *Enterococcus* species, generally accepted as safe (GRAS) *Streptococcus thermophilus*, and combinations thereof. In accordance with another preferred embodiment of the invention, the microbiological culture media can include at least one live probiotic organism selected from *Lactobacillus* species and at least one live probiotic organism selected from *Bifidobacterium* species.

Examples of suitable *Lactobacillus* species include, but are not limited to, *L. acidophilus, L. paracasei, L. fermentum, L. rhamnosus, L. johnsonii, L. plantarum, L. reuteri, L. salivarius, L. brevis, L. bulgaricus, L. helveticus, L. grasseri, L. casei, L. lactis*, and combinations thereof.

Examples of suitable *Bifidobacterium* species include, but are not limited to, *B. bifidum, B. breve, B. infantis, B. longum, B. lactis* and combinations thereof.

Examples of suitable *Enterococcus* species include, but are not limited to, *E. faceum, E. faecalis*, and combinations thereof.

While various nutraceutical or nutritive agents can be utilized in the microbiological culture media of the invention, suitable nutraceutical or nutritive agents should contribute to the production of the desired beneficial compound as well as to the stability of the microbiological media. The particular nutraceutical or nutritive agent or agents utilized in the microbiological culture media will depend upon the beneficial compound to be derived. For example, if the beneficial compound to be derived from the microbiological culture media is stabilized dihydrolipoic acid (DHLA), the nutritive agent contained in the microbiological media may be tumeric rhizome (curcuma longa). In another preferred embodiment, the nutraceutical or nutritive agent utilized in the microbiological culture media may be a synthetic form of the beneficial compound to be derived or may be naturally occurring source of the beneficial compound, such as, for example, a plant or herb, which must be processed in order to isolate the beneficial compound.

In accordance with certain preferred embodiments of the invention, a beneficial compound for use in a medicament or a nutritional supplement may be derived by preparing a microbiological culture including at least one live probiotic organism and at least one nutraceutical or nutritive agent, incubating the culture to initiate probiotic activity, harvesting a waste byproduct of the probiotic activity, and separating a beneficial compound from the waste byproduct.

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

EXAMPLES

Stabilized Dihydrolipoic Acid (DHLA)

DHLA is typically produced within the body through the redox conversion of lipoic acid or alpha-lipoic acid (ALA) during normal metabolic activity. However, the body generally only produces an amount of DHLA sufficient to assist in metabolic function. However, DHLA has been shown, at least in part, to be an effective antioxidant and chelating agent that can be utilized to scavenge reactive nitrogen species (RNS) and reactive oxygen species (ROS) such as, for example, singlet oxygen, that can contribute to a number of degradative pathological syndromes such as diabetes, glaucoma, atherosclerosis, and other neuropathies. DHLA has also been found, at least in part, to be effective to prevent or repair oxidative damage in cells and to regenerate certain important nutrients in the body such as, for example, vitamins C and E. However, there is no DHLA commercially available only ALA which is derived from non-living sources which have no DNA and may induce cellular DNA degradation especially in long term use. As a result it is believed that such ALA used in the cell to make minimal amounts of DHLA is not beneficial for long term use. Conversely, DHLA derived from once living sources includes DNA which is known to support cell DNA.

In accordance with certain preferred embodiments of the invention, stabilized dihydrolipoic acid (DHLA) for use in a medicament or nutritional supplement is derived from a once living source. In particular, the stabilized DHLA compound can be derived from a microbiological culture media including at least one live probiotic organism, R-lipoic acid, and at least one nutraceutical or nutritive agent.

Synthetic sources of alpha-lipoic acid (ALA) generally include, in equal amounts, R-lipoic acid and S-lipoic acid. However, it has been discovered, that ALA containing S-lipoic acid possesses pro-inflammatory properties which results in the formation of undesirable compounds and may detract from the function of ALA. In practice, therefore, R-lipoic acid is utilized in the microbiological culture media.

While various nutraceuticals or nutritive agents can be utilized in the microbiological culture media of the invention, suitable nutraceuticals or nutritive agents should contribute to the production of DHLA as well as contribute to the stability of the microbiological media. In accordance with certain preferred embodiments, the nutraceutical or nutritive agent can be turmeric rhizome (curcuma longa).

In practice, the microbiological culture media of the present invention can include about 40 composition weight percent of a paste including at least one live probiotic organism, about 20 composition weight percent R-lipoic acid, and about 40 composition weight percent of turmeric rhizome (curcuma longa) nutritive agent.

The stabilized dihydrolipoic acid (DHLA) of the present invention may be prepared by dispersing a microbiological culture media including at least one live probiotic organism, R-lipoic acid and at least one nutritive agent in distilled water to form a broth. The broth is then incubated at a predetermined temperature such as, for example, about 35° C. to about 40° C., for a select period of time such as, for example, about 72 to about 168 hours (i.e. about 3 to about 7 days) to induce probiotic activity. At the end of the incubation period, organic ethanol is added to the broth to halt the probiotic activity and preserve the synthesized compounds. Thereafter, the naturally derived DHLA can be separated from the broth and used to prepare a medicament or nutritional supplement.

Green Tea Polyphenols

As discussed above, green tea includes significant amounts of polyphenol compounds which have been found to be particularly potent antioxidant compounds which may effectively be utilized to reduce the incidence and severity of rheumatoid arthritis and heart disease and may inhibit or prevent certain cancers. However, green tea also includes significant levels of caffeine which when ingested can have an undesirable effect on neurological and cardiovascular processes. Furthermore, polyphenol compounds ingested via the consumption of green tea my not have an as high as desired level of bioavailability.

In accordance with certain preferred embodiments of the invention, polyphenol compounds with improved bioavailability and increased potency may be derived from a microbiological culture containing at least one live probiotic organism selected from Lactobacillus species, Bifidobacterium species, Enterococcus species, generally accepted as safe (GRAS) Streptococcus thermophilus, and combinations thereof, green tea leaves and at least one nutraceutical or nutritive agent. Advantageously, the resulting polyphenol compounds contain minimal amounts of associated compounds such as, for example, caffeine which is consumed during the incubation process.

Suitable nutritive or nutraceutical agents for use in a microbiological culture to produce polyphenol compounds having improved potency and bioavailability include, for example, green tea (Camellia sinensis) in whole leaf, chopped leaf or powdered form, one or more polyphenol concentrates and combinations thereof. Examples of suitable polyphenol concentrates for use in the present invention include epigallocatechin-3-gallate, epigallocatechin, epicatechin-3-gallate, epicatechin, catechin-3-galate, catechin and combinations thereof.

The improved polyphenol compounds of the present invention may be prepared by dispersing a microbiological culture media including at least one live probiotic organism, and at least one nutritive agent in distilled water to form a broth. The broth is then incubated at a predetermined temperature such as, for example, about 35° C. to about 40° C., for a select period of time such as, for example, about 96 to about 144 hours (i.e. about 4 to about 6 days) to induce probiotic activity. At the end of the incubation period, organic ethanol is added to the broth to halt the probiotic activity and preserve the synthesized compounds. Thereafter, the desired polyphenol compounds can be separated from the broth and used to prepare a medicament or nutritional supplement.

Vitamin B Derived Coenzymes

As discussed above, the B vitamins and their associated coenzymes are critical components in metabolic processes within the human body. Such B vitamins and their associated coenzymes are essential in order for the body to produce the necessary energy to conduct everyday life. Generally, an individual may consume sufficient levels of B vitamins or manufacture them in the small intestines. However, in cases of bowel disease, extreme stress, etc., a B supplement may be needed.

In accordance with certain preferred embodiments of the invention, high energy forms of the B vitamins and/or their associated end-chain coenzymes may be derived from a microbiological culture including at least one live probiotic organism selected from *Lactobacillus* species, *Bifidobacterium* species, *Enterococcus* species, generally accepted as safe (GRAS) *Streptococcus thermophilus*, and combinations thereof, a starting material including at least one B vitamin source, and at least one nutritive agent.

In practice the desired B vitamins and/or B vitamin derived coenzymes may be produced individually or in combination. The method of the present invention may be utilized to produce, for example, 5-methyltetrahydofolate, 5-deoxyadenosylcobalamin, pyridoxal-5-phosphate, coenzyme A, inositol hexanicotinamide, riboflavin-5-phosphate, thiamin cocarboxylase, inositol, choline, biotin and combinations thereof. Suitable starting materials include, for example, one or more sources of folic acid, vitamin B12, vitamin B6, vitamin B5, vitamin B3, vitamin B2, vitamin B1, inositol, choline, biotin and combinations thereof.

In practice, the microbiological culture may include a nutritive agent selected from the family of nutritional yeast species. One suitable nutritional yeast species for use in conjunction with the present invention includes the species *Saccharomyces cerevisiae*.

The high energy B vitamins and/or B vitamin derived coenzymes of the present invention may be prepared by dispersing a microbiological culture media including at least one live probiotic organism, at least one source of at least one B vitamin, and at least one nutritive agent in distilled water to form a broth. The broth is then incubated at a predetermined temperature such as, for example, about 35° C. to about 40° C., for a select period of time such as, for example, about 96 to about 240 hours (i.e. about 4 to about 10 days) to induce probiotic activity. At the end of the incubation period, organic ethanol is added to the broth to halt the probiotic activity and preserve the synthesized compounds. Thereafter, the desired B vitamins and/or B vitamin derived coenzymes can be separated from the broth and used to prepare a medicament or nutritional supplement.

Reduced CoQ-10 (UVI-quinol)

In accordance with certain preferred embodiments of the invention, reduced CoQ-10 may be derived from a microbiological culture including at least one live probiotic organism selected from *Lactobacillus* species, *Bifidobacterium* species, *Enterococcus* species, generally accepted as safe (GRAS) *Streptococcus thermophilus*, and combinations thereof and oxidized CoQ-10 (UVI-quinone) nutraceutical agent.

The microbiological culture of the present invention may further include one or more nutritive agents. Such nutritive agent or agents may be used to support the probiotic organism and/or improve the overall UVI-quinol yield. One such nutritive agent that is suitable for use in a microbiological culture containing at least one live probiotic organism and oxidized CoQ-10 is turmeric rhizome (*curcuma longa*) nutritive agent.

In practice, UVI-quinol may be prepared by dispersing a microbiological culture media including at least one live probiotic organism and UVI-quinone nutraceutical agent in distilled water to form a broth. The broth is then incubated at a predetermined temperature such as, for example, about 35° C. to about 40° C., for a select period of time such as, for example, about 168 to about 196 hours (i.e. about 7 to about 8.25 days) to induce probiotic activity. At the end of the incubation period, organic ethanol is added to the broth to halt the probiotic activity and preserve the synthesized compounds. Thereafter, the desired UVI-quinol can be separated from the broth and used to prepare a medicament or nutritional supplement.

Chinese Gold Coin (Herba lysimachiae)

As discussed previously, Chinese gold coin herb can be difficult for the human body to digest. Therefore, the active ingredients in the herb are not readily bioavailable or absorbable. In accordance with certain preferred embodiments of the invention, a nano-form of Chinese gold coin herb that is more readily absorbable by the human body may be derived from a microbiological culture including at least one live probiotic organism selected from *Lactobacillus* species, *Bifidobacterium* species, *Enterococcus* species, generally accepted as safe (GRAS) *Streptococcus thermophilus*, and combinations thereof and Chinese gold coin herb nutritive agent. In practice, the Chinese gold coin herb nutritive agent may be included in the microbiological culture in a whole, chopped and/or powdered form.

The nano-form of herba lysimachiae may be prepared by dispersing a microbiological culture media including at least one live probiotic organism and herba lysimachiae nutritive agent in distilled water to form a broth. The broth is then incubated at a predetermined temperature such as, for example, about 35° C. to about 40° C., for a select period of time such as, for example, about 24 to about 72 hours (i.e. about 1 to about 3 days) to induce probiotic activity. At the end of the incubation period, organic ethanol is added to the broth to halt the probiotic activity and preserve the synthesized compounds. Thereafter, the desired nano-form of herba lysimachiae can be separated from the broth and used to prepare a medicament or nutritional supplement.

While in the forgoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A method for naturally producing a medicament and/or nutritional supplement with dihydrolipoic acid comprising:

preparing a microbiological culture comprising at least one live species of microorganism capable of producing dihydrolipoic acid, R-lipoic acid, and at least one antioxidant compound;
incubating the microbiological culture to initiate microbiological activity;
halting the microbiological activity by adding ethanol;
and collecting the incubated microbiological culture including dihydrolipoic acid, wherein the antioxidant compound is a nutraceutical agent or a nutritive agent.

2. The method of claim 1, wherein the antioxidant compound comprises a nutritive agent comprising turmeric rhizome.

3. The method of claim 1, wherein the at least one live species of microorganism is selected from the group consisting of *Lactobacillus* species, *Bifidobacterium* species, *Enterococcus* species, *Streptococcus thermophilus*, and combinations thereof.

4. The method of claim 1 wherein the dihydrolipoic acid is preserved by adding ethanol to the microbiological culture.

5. The method of claim 1, wherein microorganisms present in the incubated microbiological culture consist of once-living microorganisms including dihydrolipoic acid.

6. A method for producing a medicament and/or nutritional supplement with dihydrolipoic acid, comprising the steps of:
preparing a microbiological culture containing at least one live species of microorganism capable of producing dihydrolipoic acid, R-lipoic acid, and at least one nutritive agent wherein said microbiological culture is suitable for supporting microbiological activity;
incubating said microbiological culture from about 35° C. to about 40° C. for a period of time from about 24 hours to about 240 hours;
adding ethanol to end microbiological activity and to preserve the dihydrolipoic acid in the incubated microbiological culture; and
collecting the incubated microbiological culture including said dihydrolipoic acid.

7. The method of claim 6, wherein said microbiological culture comprises at least one live species of microorganism selected from the group consisting of *Lactobacillus* species, *Bifidobacterium* species, *Enterococcus* species, *Streptococcus thermophilus*, and combinations thereof.

8. The method of claim 6, wherein said microbiological culture further comprises at least one antioxidant.

9. The method of claim 8, wherein said antioxidant is selected from the group consisting of UVI-quinone, polyphenol concentrates, tumeric rhizome, and combinations thereof.

10. The method of claim 6, wherein said nutritive agent comprises turmeric rhizome.

11. The method of claim 10, wherein said microbiological culture comprises about 20 weight percent R-lipoic acid and about 40 weight percent turmeric rhizome based on total weight of said microbiological culture.

12. The method of claim 6, wherein said microbiological culture is incubated for a period of time from about 72 hours to about 168 hours, about 96 hours to about 240 hours, about 96 hours to about 144 hours, or about 168 hours to about 196 hours.

13. The method of claim 6, wherein said microbiological culture is incubated for a period of time from about 24 hours to about 72 hours.

14. The method of claim 6, wherein said step of incubating is sufficient to induce probiotic activity.

15. The method of claim 6, wherein microorganisms present in the incubated microbiological culture consist of once-living microorganisms including dihydrolipoic acid.

16. A method for preparing a medicament or nutritional supplement including dihydrolipoic acid comprising:
preparing a microbiological culture comprising at least one live species of microorganism capable of producing dihydrolipoic acid, R-lipoic acid, and at least one antioxidant compound;
incubating the microbiological culture to initiate microbiological activity;
halting microbiological activity by adding ethanol;
collecting the incubated microbiological culture; and
preparing a medicament or nutritional supplement comprising the dihydrolipoic acid,
wherein the antioxidant compound is a nutraceutical agent or a nutritive agent, and wherein microorganisms present in the incubated microbiological culture consist of once-living microorganisms including dihydrolipoic acid.

17. The method of claim 16, wherein said microbiological culture comprises at least one live species of microorganism selected from the group consisting of *Lactobacillus* species, *Bifidobacterium* species, *Enterococcus* species, *Streptococcus thermophilus*, and combinations thereof.

18. The method of claim 16, wherein said antioxidant is selected from the group consisting of UVI-quinone, polyphenol concentrates, tumeric rhizome, and combinations thereof.

19. The method of claim 18, wherein said antioxidant comprises turmeric rhizome.

20. The method of claim 16 comprising preparing a nutritional supplement.

21. The method of claim 20, wherein said microbiological culture comprises about 20 weight percent R-lipoic acid and about 40 weight percent turmeric rhizome based on total weight of said microbiological culture.

22. The method of claim 16, wherein said microbiological culture is incubated for a period of time from about 24 hours to about 72 hours.

23. A method for naturally producing a medicament and/or nutritional supplement with dihydrolipoic acid consisting of:
preparing a microbiological culture comprising at least one live species of microorganism capable of producing dihydrolipoic acid, R-lipoic acid, and at least one antioxidant compound;
incubating the microbiological culture to initiate microbiological activity;
ending the microbiological activity by adding ethanol; and
collecting the incubated microbiological culture including dihydrolipoic acid,
wherein the antioxidant compound is a nutraceutical agent or a nutritive agent.

24. The method of claim 23, wherein said microbiological culture comprises at least one live species of microorganism selected from the group consisting of *Lactobacillus* species, *Bifidobacterium* species, *Enterococcus* species, *Streptococcus thermophilus*, and combinations thereof.

25. The method according to claim 23, wherein said antioxidant comprises turmeric rhizome.

26. The method of claim 24, wherein said microbiological culture comprises about 20 weight percent R-lipoic acid and about 40 weight percent turmeric rhizome based on total weight of said microbiological culture.

27. The method of claim 23, wherein said microbiological culture is incubated for a period of time from about 24 hours to about 72 hours.

28. The method of claim 23, wherein microorganisms present in the incubated microbiological culture consist of once-living microorganisms including dihydrolipoic acid.

* * * * *